(12) United States Patent
Cox

(10) Patent No.: US 6,592,104 B2
(45) Date of Patent: Jul. 15, 2003

(54) SCENT DISPENSER AND METHOD

(76) Inventor: Larry R. Cox, 5540 Sullivantown Rd., Walkertown, NC (US) 27051

( * ) Notice: Subject to any disclaimer, the term of this patent is extended or adjusted under 35 U.S.C. 154(b) by 0 days.

(21) Appl. No.: 09/917,083

(22) Filed: Jul. 30, 2001

(65) Prior Publication Data

US 2003/0020185 A1 Jan. 30, 2003

(51) Int. Cl.[7] .................................................. B01F 3/04
(52) U.S. Cl. .................... 261/26; 261/30; 261/DIG. 88; 422/124; 43/1
(58) Field of Search ...................... 261/26, 30, DIG. 88; 422/124; 43/1

(56) References Cited

U.S. PATENT DOCUMENTS

| | | | |
|---|---|---|---|
| 2,556,608 A | 6/1951 | Will | |
| 2,738,225 A | 3/1956 | Meek | |
| 3,046,192 A | 7/1962 | Bilyeu | |
| 4,472,377 A | 9/1984 | Teranishi et al. | |
| 4,506,806 A | 3/1985 | Lincoln et al. | |
| 4,523,717 A | 6/1985 | Schwab | |
| 4,609,245 A | 9/1986 | Sakschek | |
| 4,667,430 A | 5/1987 | Ziese, Jr. | |
| 4,771,563 A | 9/1988 | Easley | |
| 4,773,177 A | 9/1988 | Gray, II | |
| 4,788,787 A | 12/1988 | Konietzki | |
| 4,830,791 A * | 5/1989 | Muderlak et al. | 239/35 |
| 4,860,488 A | 8/1989 | Shigetoyo | |
| 4,944,940 A | 7/1990 | Christenson, II | |
| 4,953,763 A | 9/1990 | Kierum | |
| 4,989,547 A | 2/1991 | Eaton | |
| 5,094,025 A | 3/1992 | Daniels | |
| 5,105,133 A * | 4/1992 | Yang | 261/DIG. 88 |
| 5,148,949 A | 9/1992 | Luca | |
| 5,168,654 A | 12/1992 | Chien | |
| 5,282,334 A | 2/1994 | Kimura et al. | |
| 5,299,376 A | 4/1994 | Roberts | |
| 5,305,541 A | 4/1994 | Simpson | |
| 5,335,446 A | 8/1994 | Shigetoyo | |
| 5,369,903 A | 12/1994 | Cox | |
| 5,566,502 A | 10/1996 | Shigetoyo | |
| 5,678,763 A | 10/1997 | Scheuer | |
| 5,884,808 A * | 3/1999 | Muderlak et al. | 222/1 |
| 6,050,016 A | 4/2000 | Cox | |
| 6,085,989 A | 7/2000 | Cox | |
| 6,241,218 B1 * | 6/2001 | Tanitomi | 261/104 |

OTHER PUBLICATIONS

Drawings from pending patent Ser. No. 29/125,687 filed Jun. 28, 2000 by inventor Larry R. Cox.

* cited by examiner

*Primary Examiner*—Robert A. Hopkins

(57) ABSTRACT

A portable, convenient scent dispenser and method of operation allows the user to quickly change scents used therein as desired while hunting. A scent receptacle mounted in the lower end of a cylindrical housing is removable for replacing or exchanging scented materials. The scent dispenser provides a cylindrically-shaped housing having a removable cap containing microcontrolled electrical circuitry which includes mode indicators and a select switch. The lower body of the housing contains a battery assembly and an electric fan. The scent dispenser can be manually, selectively operated in a variety of modes to allow the fan to run continuously, cyclically, or cyclically only during daylight hours for economical power consumption.

15 Claims, 4 Drawing Sheets

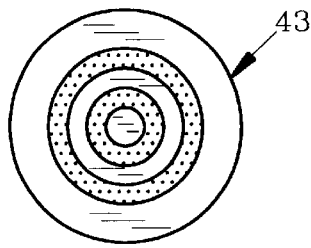
FIG. 5
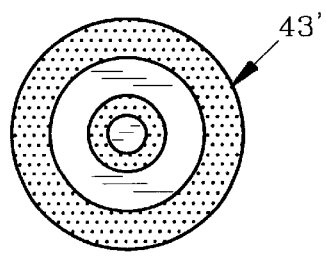
FIG. 6
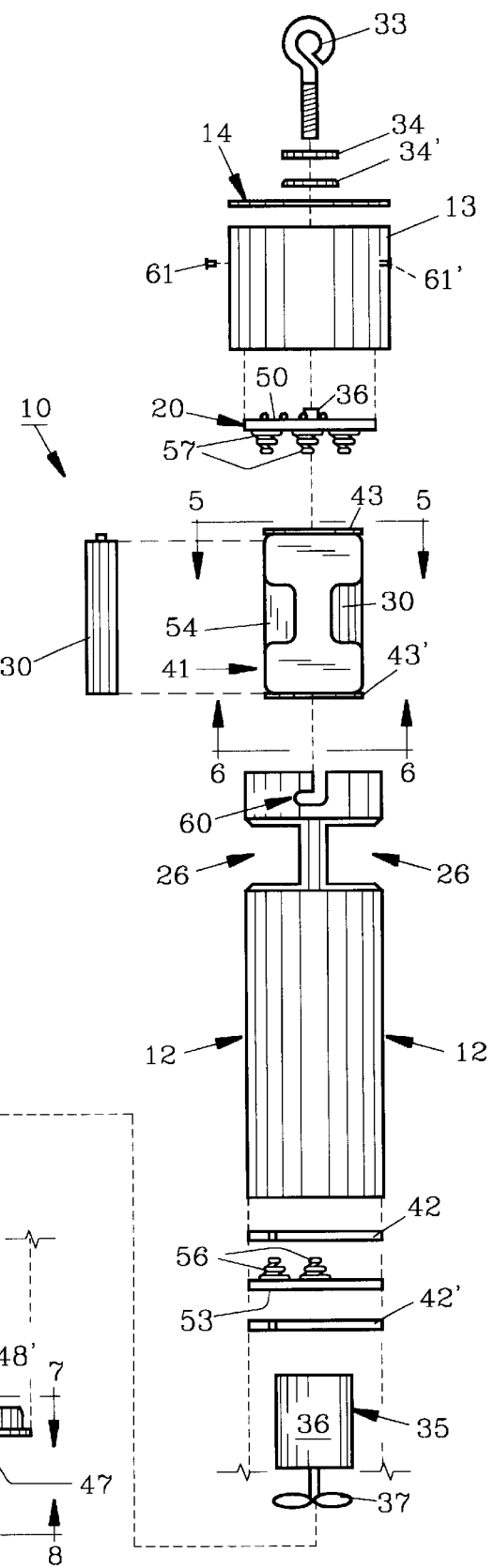
FIG. 3
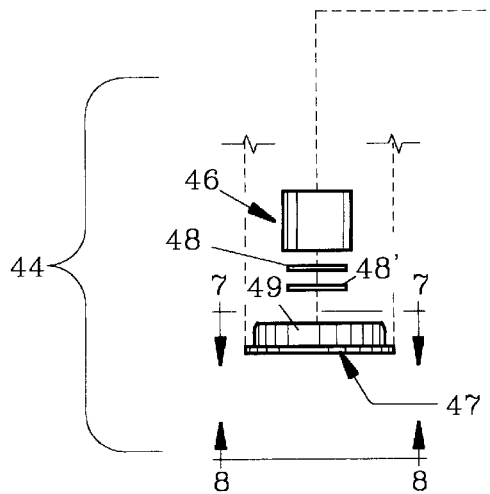

US 6,592,104 B2

SCENT DISPENSER AND METHOD

FIELD OF THE INVENTION

The invention herein pertains to a scent dispenser for luring deer or the like and in particular pertains to a scent dispenser which utilizes microcontroller circuitry for selective operation of a fan which forces air past a contained, conventional scent-producing material for scent distribution into the surrounding atmosphere.

DESCRIPTION OF THE PRIOR ART AND OBJECTIVES OF THE INVENTION

Various mechanical and electrical scent-dispensing devices have been used in the past by hunters, photographers and others to attract deer and other game. These devices are generally suspended from tree limbs or are otherwise advantageously positioned for the best results. Certain of the prior art devices are large and bulky, requiring special care during handling and transportation. Other electrical prior art devices must be turned on manually while hunting and thereafter turned off to terminate power consumption to prevent battery depletion. Other known prior art devices are mechanical in nature and continually dispense a scent until removed or the scent is exhausted. Certain of the more recent scent dispensers have complex electrical circuitry and are expensive to manufacture and are difficult to operate.

Thus, with the problems and disadvantages of traditional scent dispensers, the present invention was conceived and one of its objectives is to provide a microcontrolled scent dispenser and method which allows a variety of operational modes, depending on the particular needs of the user.

It is another objective of the present invention to provide a scent dispenser which includes a programmed microcontroller which provides precise cycles of operation.

It is yet another objective of the present invention to provide a scent dispenser which allows a variety of scent-producing materials to be easily loaded and replaced.

It still another objective of the present invention to provide a scent dispenser which can be conveniently carried on a person due to its compact cylindrical shape.

It is a further objective of the present invention to provide a scent dispenser which includes electrical circuitry for selective operation in either continuous, cyclic, or cyclic daylight operation.

It is also an objective of the present invention to provide a scent dispenser which has an impact and weather resistant housing which shields the operating components from inclement weather while allowing sufficient airflow for proper operation of the internal electric fan.

It is yet still another objective of the present invention to provide a scent dispensing device having a potentiometer which can be manually adjusted to control the fan run time during cyclic operations.

It is also an objective of the present invention to provide a scent dispenser which can utilize a variety of scent producing materials and which has a control panel mounted on the housing for easy visibility and operation by the use of flashing LEDs.

Various other objectives and advantages of the present invention will become apparent to those skilled in the art as a more detailed description is set forth below.

SUMMARY OF THE INVENTION

The aforesaid and other objectives are realized by providing a scent dispenser housing having a generally cylindrical shape. The housing has a larger diameter upper cylinder or cap which is rotatably removable and which includes a control panel. An air channel is defined between it and the lower, smaller diameter cylinder or body for incoming fresh air. Mounted in the cap is a logic board with a microcontroller which manages the scent operation. The housing lower body contains a battery assembly and a fan. A scent receptacle resides in the lower body which can be easily removed for loading or replacing scented materials.

The method of using the scent dispenser includes manually depressing a select switch from the control panel which illuminates, in advancing fashion, a series of LEDs which indicate particular modes of operation, such as "off", "continuous", "cyclic" and "daylight" operation. By successively pressing the select switch, illumination of the LEDs for the various modes advances. A potentiometer connected to the circuit board can be manually adjusted to vary the run time of the fan. Ambient light is sampled once per minute by the photocell which directs the microcontroller to activate the fan, depending of the level of light received and the mode selected.

BRIEF DESCRIPTION OF THE DRAWINGS

FIG. 3 provides a reduced exploded elevational view of the scent dispenser with the components removed;

FIG. 5 shows an enlarged top plan view of the printed circuit board of the battery assembly as seen in FIG. 3 along lines 5—5;

FIG. 6 pictures an enlarged bottom plan view of the printed circuit board of the battery assembly along lines 6—6 as shown in FIG. 3;

DETAILED DESCRIPTION OF THE PREFERRED EMBODIMENTS AND OPERATION OF THE INVENTION

Figure 1:
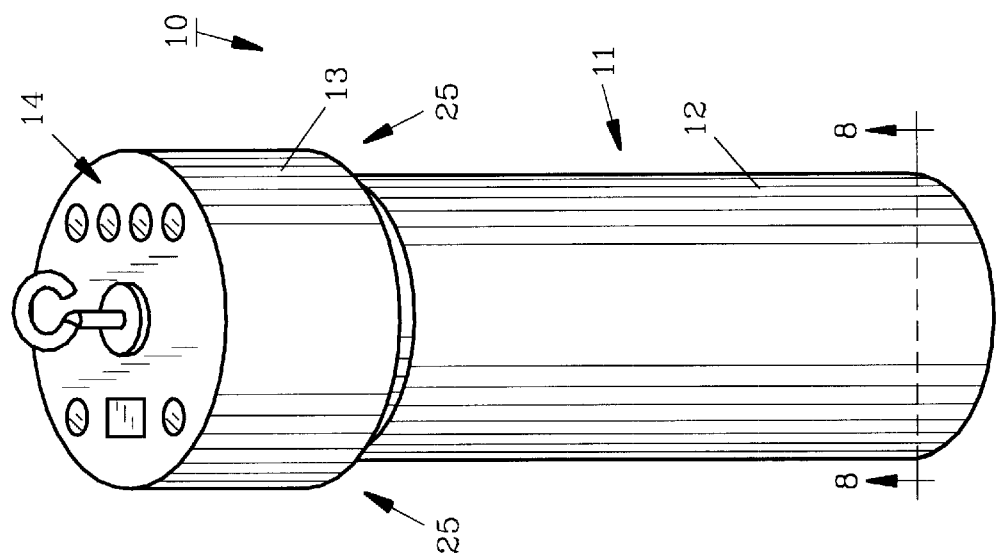
FIG. 1 shows a top, front perspective view of the preferred scent dispenser of the invention.

For a better understanding of the invention and its operation, turning now to the drawings, FIG. 1 demonstrates preferred scent dispenser 10 for luring game which includes cylindrical housing 11 with a smaller diameter lower cylinder or body 12 joined to upper cylinder or cap 13 which has a somewhat larger diameter. Cylinders 12 and 13 are each formed from suitable, durable, rigid polymeric materials preferably by conventional molding or extruding. Body 12 is preferably approximately 4.75 cm in width and 14.5 cm in length, whereas cylinder 13 is preferably approximately 5.5 cm in width and 4 cm in length for convenience in carrying and storing. Body 12 includes a pair of opposing reversed L-shaped slots 60, 60' (60' not seen) in FIG. 3 which receive cap posts 61, 61' respectively. Cap 13 can be easily, rotatably removed from body 12 for supplying fresh batteries 30 as needed. Housing 11 provides an air channel 25 for entry of fresh air which is drawn between body 12 and cap 13 by fan 35. The incoming fresh air then passes through openings 26 in body 12 (FIG. 3) and past motor 36 for cooling. The air exits housing 11 through aperture 49 of end cap 47 (FIG. 7) after collecting scents as it passes scent receptacle 45 where it will attract surrounding game.

Figure 2:
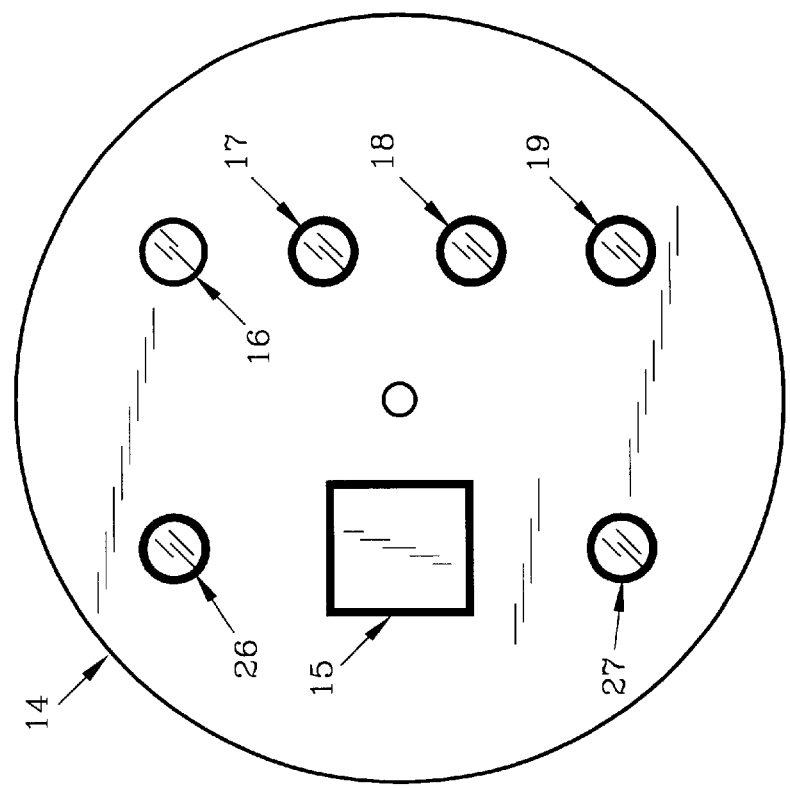
FIG. 2 illustrates an enlarged view of the control panel as shown in FIG. 1 removed from the dispenser cap.
Figure 4:
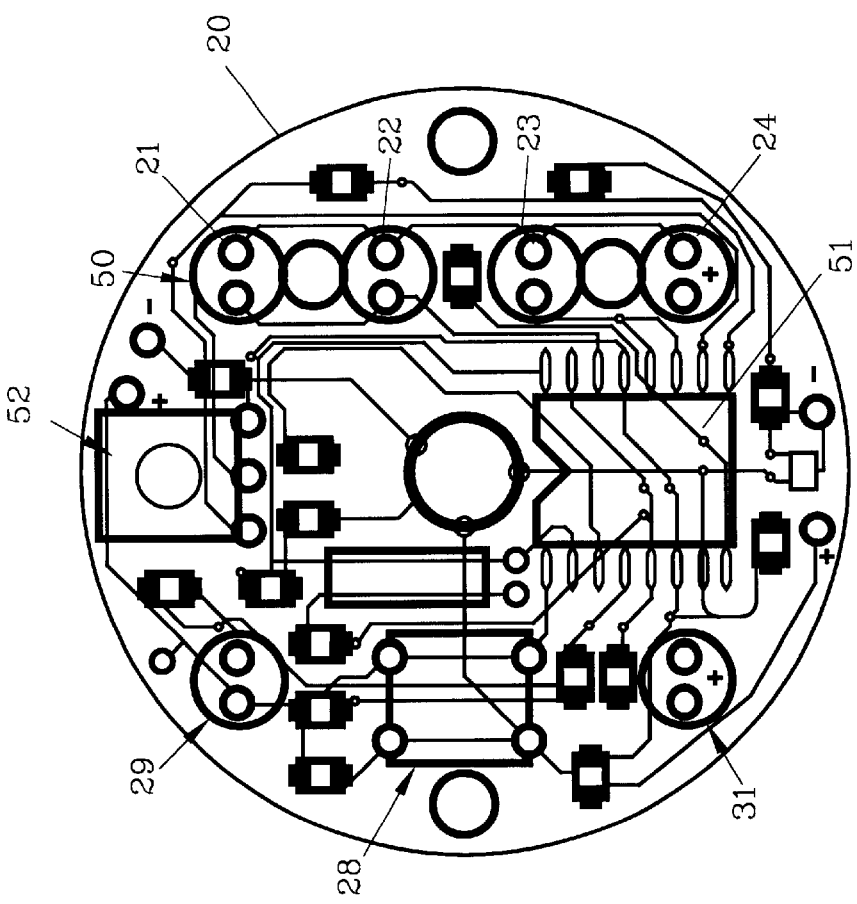
FIG. 4 depicts an enlarged schematic representation of the logic circuitry.

Control panel 14 seen enlarged in FIG. 2 is positioned atop cap 13 and provides convenience to the user in operational choices as managed by microcontroller 51 (FIG. 4) in logic circuitry 50 on logic board 20. Mode select switch 28 can be pushed (by urging area 15 on control panel 14) repeatedly to select the desired mode, such as "off" shown at LED window 16 as LED 21 (FIG. 4) is activated, "continuous operation" shown at LED window 17, by LED 22, "cyclic operation" shown at LED window 18 by LED 23 or "daylight fan operation" shown at LED window 19 by LED 24. As would be understood, windows 16–19 are transparent and are illuminated by LEDs 21–24 therebeneath shown schematically in FIGS. 2 and 4. Control panel 14 is a thin plastic film which provides transparent windows 16–19 for LEDs 21–24 and 26, 27 to be seen therethrough. By subsequent pushing of select switch 28 through area 15, the various modes are visible by LEDs 21–24 which are activated (advanced) in turn. Control panel 14 further provides transparent window 26 which allows light to strike photocell 29 as shown in FIG. 4, and transparent window 27 which allows LED 31 to be seen when low battery voltage is sensed when "AA" batteries 30, as shown in FIG. 3 need replacing. Only two (2) batteries 30 of four (4) required are illustrated.

Battery assembly 41 (FIG. 3) contains four "AA" size batteries and includes top circuit board 43 and bottom circuit board 43', also seen in FIGS. 5 and 6 connected thereto. Top circuit board 43 and lower circuit board 43' are mounted on opposite ends of plastic battery magazine 54, which maintains the four "AA" batteries. Electricity passes from batteries 30 through top circuit board 43, through conductor springs 57 on logic board 20 to power logic circuitry 50 thereon. Electricity from battery assembly 41 also is directed to drive fan 35 as bottom circuit board 43' transfers electricity from batteries 30 to conductor springs 56 on circuit board 53 to supply power to fan 35 through electrical contacts (not seen) on fan motor 36. Conductor springs 56, 57 insure reliable electrical connections during windy and other adverse conditions.

Figure 8:
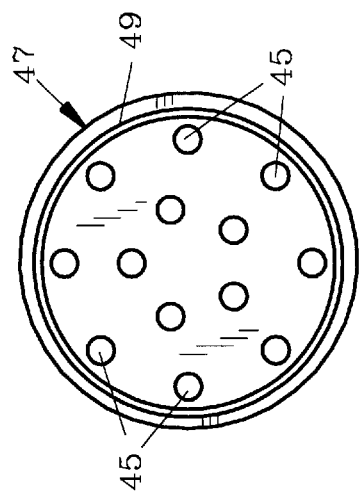
FIG. 8 features an enlarged bottom view of the scent dispenser along lines 8—8 of FIG. 1 with the scent receptacle removed.

In FIG. 3, preferred scent dispenser 10 is illustrated in an exploded view with eye bolt 33, sealing washer 34 and o-ring 34' removed. Eye bolt 33 is rotated into threaded socket 36 positioned on logic board 20 having logic circuitry 50 thereon. Eye bolt 33 thus secures logic board 20 in cap 13 of housing 11 while washer 34 and o-ring 34' prevents moisture entry. Preferably four (4) AA batteries 30 drive conventional DC-powered fan 35 having a 4 ma motor 36 as manufactured by Johnson Electric North America, Inc. of Shelton, Conn. seen with four (4) conventional plastic fan blades 37 seen in FIG. 8. Resilient retaining rings 42, 42' also seen in FIG. 3 are formed from plastic and allow for quick insertion (or removal) and secure positioning of fan 35 within lower cylindrical body 12 of housing 11.

Figure 7:
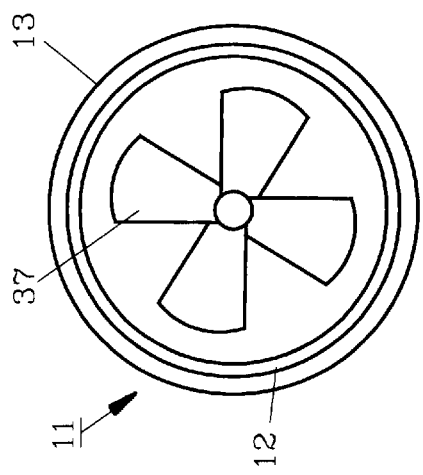
FIG. 7 demonstrates an enlarged top plan view of the assembled scent receptacle as removed from the scent dispenser along lines 7—7 of FIG. 3.

As further shown in FIGS. 3 and 7, scent receptacle 44 which is preferably molded from a suitable plastic includes removable cup 46 for containing an absorbent material (not shown) such as a sponge, cotton or the like which is preferably saturated with a standard available scent producing liquid or gel. Solid or powdered scent producing materials can also alternately be used without an absorbent material. Hook and loop patches 48, 48' allow cup 46 to be secured in place or removed as desired from base 47. Base 47 of scent receptacle 44 is a circular disk preferably molded with friction ring 49 which tightly engages the lower inner walls of cylinder 12 of housing 11 to hold scent receptacle 44 in place during use. Apertures 45 allow air from fan 35 to blow over scent receptacle 44 and outwardly into the surrounding environment for scent dispensing and game luring during hunting activities.

The preferred method of operation of scent dispenser 10 can be described as follows: Scent receptacle 44 is manually removed from scent dispenser 10 and a suitable, commercially available liquid, gel, powder or other scent generating material is positioned in cup 46. Cotton or other absorbent material is preferably used with a liquid or gel to maintain the same within cup 46. Cup 46 is then reattached to base 47 preferably with hook and loop patches 48, 48' though other attaching means may be employed. Thereafter, scent receptacle 44 is reinserted into housing 11. Next, control panel 14 is then used to manually select a particular mode of operation. By pressing site 15 on panel 14 with a finger mode select switch 28 is activated and by continuously pressing as needed, four (4) modes (off, continuous operation, cyclic operation or daylight operation) are available. With a desired mode selected, scent dispenser 10 is then suspended from a tree limb or otherwise by placing a cord or wire from the limb through eye bolt 33 and securing the same. Thereafter the contained scent is dispensed by fan 35 as it blows air into the surrounding atmosphere and environment through aperture 45, attracting deer or other game, depending on the particular desire of the user.

During mode selection, as mode select switch 28 is pressed, one time programmable microcontroller 51 (FIGS. 4 and 9) as manufactured by Motorola, Inc. of Phoenix, Ariz. 85036 as part No. MC68HC705 KJ1 is so programmed whereby LED 21 is first illuminated and can be seen through window 16 showing scent dispenser 10 as "off" and not operating. By depressing mode select switch 28 again, "continuous run" LED 22 is illuminated as seen through window 17 whereby fan 35 now runs continuously until scent dispenser 10 is either turned off or batteries 30 sufficiently weaken. Test have shown that in continuous mode scent dispenser 10 will operate for about seven days before battery failure. If the continuous operation mode is not desired, mode select switch 28 can be again pressed and LED 23 will illuminate, demonstrating that scent dispenser 10 is in the cyclic mode. This cyclic mode saves energy in that fan 35 runs for thirty seconds and then shuts off for thirty seconds, constantly until such time as the "off" mode is selected or until batteries 30 sufficiently weaken. Test have shown that scent—dispenser 10 will operate in the cyclic mode for about two weeks before battery failure. Standard potentiometer 52 can be manually adjusted to vary the run time of fan 35 as explained further below.

For hunters that desire operation and scent dispensing only during daylight hours, mode select switch 28 can be pressed and released until LED 24 is illuminated depicting "daylight only" operation. In this mode preferred cadmium sulfide photocell 29 as manufactured by Clairex Technologies, Inc. of Plano, Tex. 75074, as part No. CDST18, senses daylight through window 26 on control panel 14. Microcontroller 51 on circuit board 20 then provides for cyclic fan operation, but only during daylight hours.

As an additional feature, LED 31 flashes to demonstrate that batteries 30, which consist preferably of four (4) size AA batteries, need replacing. In order to further conserve energy, mode indicating LEDs 21–24 and LEDs 29–31 when activated, automatically turn off after four seconds.

Figure 9:
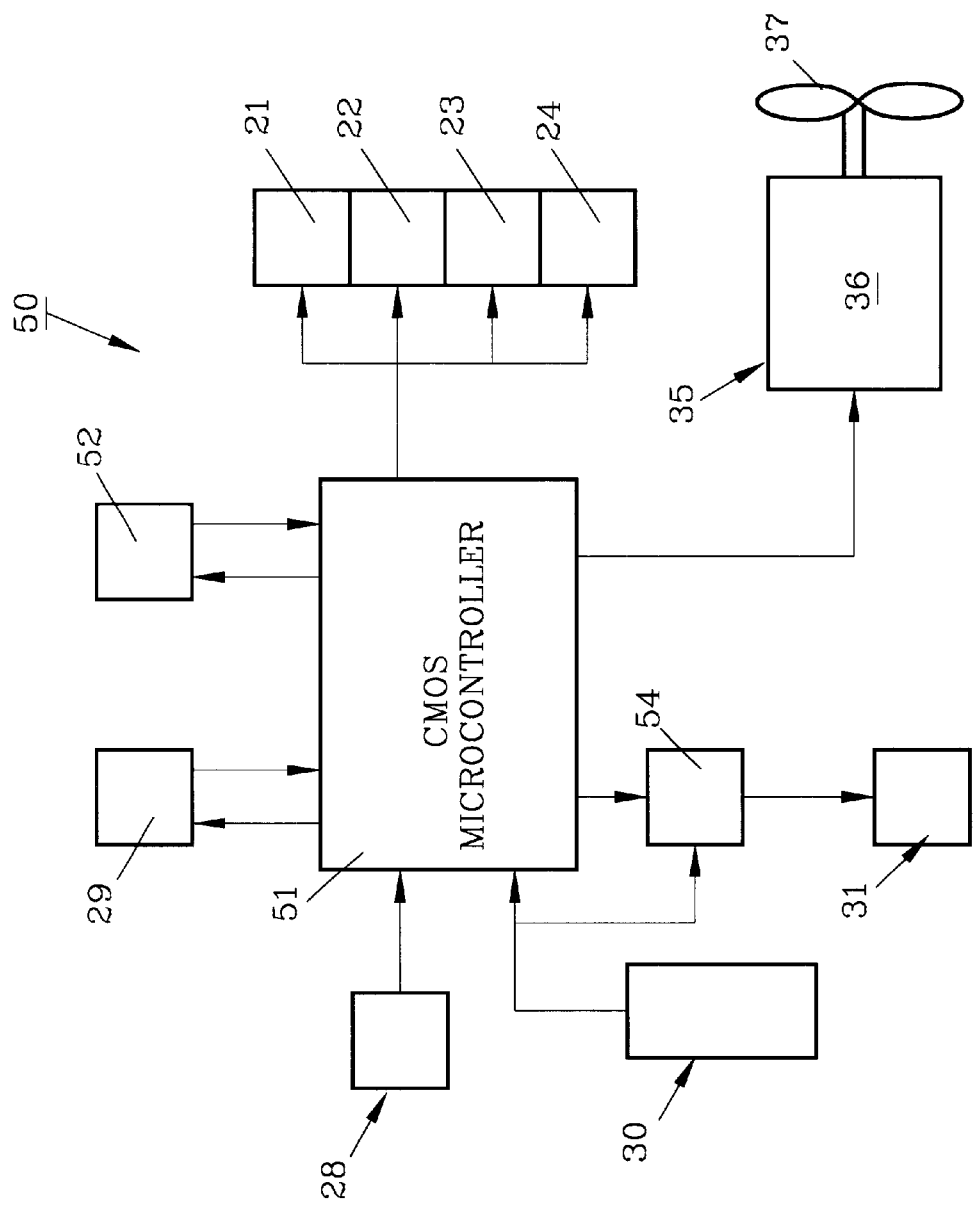
FIG. 9 illustrates a schematic block diagram of the electrical circuitry.

In FIG. 9, a schematic block diagram of preferred logic circuitry 50 is shown. Conventional Motorola CMOS microcontroller 51 is seen connected to conventional photocell 29 (also seen in FIG. 4). Potentiometer 52 is also electrically connected to microcontroller 51 which allows manual adjustment of the length of run time for each one minute cycle of fan motor 36 during the "cyclic operation" of scent dispenser 10. Fan motor 36 can be set to run from 0% to 100% of each one-minute cycle as desired by the user, by manually turning the slotted head of an adjusting bolt (not seen) on standard potentiometer 52.

Voltage detector 54 tests batteries 30 when fan motor 36 is running and for two seconds thereafter. Voltage detector 54 also tests batteries 30 when scent dispenser 10 is in the "off" mode. When a low battery condition is detected, LED 31 will then flash once per second indicating a weak battery condition. As earlier stated, pressing select switch 28 advances the operation mode one step at a time, as visually indicated by LEDs 21, 22, 23 and 24.

The illustrations and examples provided herein are for explanatory purposes and are not intended to limit the scope of the appended claims.

I claim:

1. A scent dispenser comprising:
    a cylindrically shaped housing, a scent receptacle, said scent receptacle contained within said cylindrically shaped housing, logic circuitry, a microcontroller, said microcontroller connected to said logic circuitry, a fan, said fan connected to said logic circuitry, whereby said fan is controlled by said microcontroller to selectively force air across said scent receptacle and discharge the scented air.

2. The scent dispenser of claim 1 wherein said housing comprises a cap, a body, said cap releasably joined to said body.

3. The scent dispenser of claim 1 wherein said housing is cylindrically shaped.

4. The scent dispenser of claim 1 further comprising a control panel, said control panel positioned on said housing.

5. The scent dispenser of claim 1 further comprising a means to secure said fan within said housing, said securing means comprising a retaining ring.

6. The scent dispenser of claim 1 further comprising a logic board, said logic board containing said logic circuitry, a threaded socket, said threaded socket mounted on said logic board, said threaded socket for engaging an eye bolt, said eye bolt passing through said housing for engaging said threaded socket.

7. The scent dispenser of claim 1 wherein said scent receptacle comprises a cup, a base, said cup releasably attached to said base, said base defining an aperture, said aperture to allow fluid communication from within said housing to the surrounding environment.

8. The scent dispenser of claim 7 further comprising a hook and loop fastener, said hook and loop fastener affixed to said base.

9. The scent dispenser of claim 1 wherein said housing comprises a cap, a body, said body defining a slot, a post, said post mounted on said cap, said post positionable within said slot for releasably affixing said cap to said body.

10. A scent dispenser comprising:
    a housing, logic circuitry, said circuitry contained within said housing, a microcontroller, said microcontroller connected to said logic circuitry, a power supply, a fan, said power supply connected to logic circuitry and to said fan to drive the same, said fan and said power supply contained within said housing, a retaining ring, said retaining ring attached to said fan to secure said fan within said housing, a switch, said switch connected to said logic circuitry, said switch for selecting an operation mode, a scent receptacle, said scent receptacle proximate said fan to enable the fan to drive air past said scent receptacle and from said housing.

11. The scent dispenser of claim 10 further comprising a control panel, said control panel mounted on said housing contiguous said logic circuitry.

12. A method of utilizing a scent dispenser having a housing containing logic circuitry with mode indicators and a mode indicator switch to selectively operate a fan which forces air within said housing over a scent receptacle and from said housing, comprising the steps of:
    a) securing the fan within the housing with a retaining ring;
    b) loading the scent receptacle with a scented material;
    c) positioning the scent dispenser at a desired location;
    d) selecting an operating mode to activate the fan; and
    e) dispensing the scent by said fan.

13. The method of claim 12 wherein loading the scent dispenser comprises the steps of:
    a) removing the scent receptacle from the housing;
    b) placing scented material therein; and
    c) replacing the loaded scent receptacle within the housing.

14. The method of claim 12 wherein selecting a particular operating mode comprises the step of selecting one of the following modes:
    a) off;
    b) continuous fan operation;
    c) cyclic fan operation; or
    d) daylight fan operation.

15. The method of claim 14 wherein selecting the daylight fan operation mode comprises the step of activating the fan utilizing a photocell.

* * * * *